US007359176B2

United States Patent
Miyaishi et al.

(10) Patent No.: US 7,359,176 B2
(45) Date of Patent: Apr. 15, 2008

(54) BOARD FOR ION GENERATION AND ION GENERATING APPARATUS

(75) Inventors: Manabu Miyaishi, Shiga (JP); Takeshi Ogawa, Shiga (JP); Yoshihiro Ushio, Shiga (JP); Masakazu Yasui, Shiga (JP); Nobuyuki Tanaka, Shiga (JP)

(73) Assignee: Kyocera Corporation, Kyoto (JP)

( * ) Notice: Subject to any disclaimer, the term of this patent is extended or adjusted under 35 U.S.C. 154(b) by 471 days.

(21) Appl. No.: 11/066,503

(22) Filed: Feb. 24, 2005

(65) Prior Publication Data

US 2005/0231884 A1 Oct. 20, 2005

(30) Foreign Application Priority Data

Feb. 25, 2004 (JP) ............................ P2004-050328

(51) Int. Cl.
*H02T 23/00* (2006.01)

(52) U.S. Cl. ...................................... 361/232
(58) Field of Classification Search ................ 361/231, 361/232
See application file for complete search history.

(56) References Cited

U.S. PATENT DOCUMENTS 4,391,773 A * 7/1983 Flanagan ...................... 422/22
5,348,571 A * 9/1994 Weber ............................ 96/68

FOREIGN PATENT DOCUMENTS

JP 2003-036955 2/2003

\* cited by examiner

*Primary Examiner*—Ronald W. Leja
(74) *Attorney, Agent, or Firm*—Hogan & Hartson LLP

(57) ABSTRACT

Provided is a board for ion generation that is capable of generating negative ions with much better efficiency and in an amount larger than that of positive ions. In the board for ion generation, a discharge electrode is formed on one principal surface of a substrate formed of ceramics, an induction electrode is formed on another principal surface of the substrate, the discharge electrode and the induction electrode being disposed opposite to each other, a first protective layer and a second protective layer are formed so as to cover the discharge electrode and the induction electrode, respectively. Surface discharge is generated on a surface of the first protective layer by applying an AC voltage between the discharge electrode and induction electrode, and positive ions and negative ions are alternately generated in the air. In the board for ion generation, the porosity of the substrate is 5 to 10 vol. %.

11 Claims, 6 Drawing Sheets

BOARD FOR ION GENERATION AND ION GENERATING APPARATUS

BACKGROUND OF THE INVENTION

1. Field of the Invention

The present invention relates to a board for ion generation that is capable of generating negative cluster ions with higher efficiency and an ion generating apparatus using the same.

2. Description of the Related Art

An ion generating apparatuses used for disinfection and deodorization has recently attracted attention and such apparatuses have started finding application in various types of electric apparatuses such as air purifiers, air conditioners, refrigerators and hair driers. There is known as such an ion generating apparatus using a board for ion generation having such a structure that electrodes are formed so that a dielectric body is sandwiched therebetween (see, for example, Japanese Unexamined Patent Publication JP-A 2003-36955, pages 5-6).

A conventional board for ion generation that has been used in such an ion generating apparatus will be described below using a cross-sectional view shown in FIG. 5. As shown in FIG. 5, a conventional board 101 for ion generation has generally been fabricated by a ceramic green sheet stacking method. A grid-like discharge electrode 102 comprising tungsten (W) as a main component is formed on one principal surface of a dielectric body 105 formed of alumina ceramics or the like. A flat induction electrode 103 also comprising tungsten as the main component is formed on the other principal surface of the dielectric body 105. Further, a first protective layer 106a for covering the surface of the discharge electrode 102 is provided on the one principal surface of the dielectric body 105 and a second protective layer 106b for covering the surface of the induction electrode 103 is provided on the other principal surface of the dielectric body 105.

Surface discharge directed from a surface part of the first protective layer 106a forming a zone above the discharge electrode 102 toward a discharge section 106a-A in a surface of the first protective layer 106a forming a zone above the end of the induction electrode 103 and surface discharge directed from the discharge section 106a-A in a surface forming the zone above the end of the induction electrode 103 toward the surface part of the first protective layer 106a forming a zone above the discharge electrode 102 are alternately and repeatedly generated on the surface of the first protective layer by applying an AC voltage to those discharge electrode 102 and induction electrode 103. Positive ions and negative ions, thereby, are generated in the zones where the surface discharge is generated, and positive and negative cluster ions are generated by surrounding the generated ions by $H_2O$ molecules. The positive and negative cluster ions produce active hydrogen peroxide ($H_2O_2$) and hydroxyl radicals (.OH) by chemical reactions and kill bacteria present in the air. Moreover, negative cluster ions take away hydrogen (H) from harmful substances (for example, substances producing bad odor or substances harmful for the health, such as nitrogen oxides), thereby deodorizing the air or making it harmless.

The first and second protective layers 106a, 106b are provided to prevent the discharge electrode 102 and induction electrode 103 from evaporation and volume loss due to a large amount of heat generated locally during the discharge. The first and second protective layers 106a, 106b may be formed of the same material as the dielectric body 105 or may be formed of a material, for example, a glassy material, different from that of the dielectric body 105.

The ion generating apparatus comprising such a conventional board 101 for ion generation generates positive and negative ion clusters in the air by the above-described surface discharge, kills bacteria and the like floating in the air, and renders harmful substances harmless. However, negative cluster ions are considered to also have an effect of making a person feel relaxed.

Accordingly, such ion generating apparatuses have recently found application for disinfecting, deodorizing and purifying the air in restricted spaces where the air can easily become stagnant, for example, business offices and conference rooms. Furthermore, a demand has been created for increased efficiency of ion generation and apparatuses capable of generating a larger number of negative cluster ions that produce a relaxing effect on humans. To meet this demand a technology is disclosed (see JP-A 2003-36955, pages 5-6) by which the grid spacing of the discharge electrode 102 is reduced to below the prescribed value and, at the same time, the thickness of the dielectric body 105 is increased to above the prescribed value in order to generate a lager number of negative cluster ions in the conventional board 101 for ion generation.

The ratio of increase in the number of generated negative cluster ions with respect to the number of generated positive cluster ions created by the board 101 for ion generation described in JP-A 2003-36955, pages 5-6, is known to be in the order of ten-odd percent to several tens of percent. Further, when negative ions are generated, the sine waveform of the AC voltage may be biased to the negative voltage side by using an electric circuit, as shown by a graph in FIG. 6 and the target atmosphere can be obtained by appropriately switching the mode of ion generation.

However, though positive cluster ions demonstrate a disinfecting and deodorizing effect by chemically reacting with bacteria and harmful substances and taking oxygen away from them, such cluster ions are known to be harmful to human health. In order to enhance further the relaxing effect of negative cluster ions on humans, the ratio of the number of generated negative cluster ions to the number of generated positive cluster ions has to be further increased. The inventors attempted to increase the number of generated negative ions with respect to that of positive ions by studying the shape and arrangement of electrodes, magnitude of applied voltage, material of dielectric body and the like, but it has been found that the increase ratio was at maximum about several tens of percent, and that further improvements will be needed to increase the relaxing effect.

Further, biasing the sine waveform to the further negative voltage side in order to generate negative ions has resulted in such drawbacks that the maximum negative voltage value increased and the amount of generated harmful ozone ($O_3$) increased accordingly.

SUMMARY OF THE INVENTION

Hence, the invention has been created in view of the above-described problems, and it is an object thereof to provide a board for ion generation that is capable of generating negative ions with good efficiency in an amount higher than that of positive ions or a board for ion generation capable of reducing the content ratio of positive ions and to provide an ion generating apparatus comprising such a board for ion generation.

The invention provides a board for ion generation, comprising:

a substrate formed of ceramics;

a discharge electrode formed on one principal surface of the substrate;

an induction electrode formed on another principal surface of the substrate;

a first protective layer formed so as to cover the discharge electrode on the one principal surface of the substrate; and a second protective layer formed so as to cover the induction electrode on the other principal surface of the substrate, wherein the discharge electrode and the induction electrode are disposed opposite to each other, wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and thereby positive ions and negative ions are generated in the air, and wherein porosity of the substrate is 5 to 10 vol. %.

Further, in the invention, an ion generation section composed of the discharge electrode and induction electrode is formed in a first region of the substrate, a positive ion adsorption section is formed in a region adjacent to the ion generation section of the substrate, and the positive ion adsorption section is composed of an electrostatic electrode provided on the one principal surface of the substrate, the electrostatic electrode having one surface exposed and being charged negatively and a counter electrode provided on the other principal surface of the substrate and charged positively.

Further, in the invention, the electrostatic electrode is formed from a plurality of conductors of a same shape or a conductor formed to have a net-like shape.

Further, in the invention, the electrostatic electrode has a plurality of protrusions formed on the one surface thereof.

Further, the invention provides an ion generating apparatus comprising the aforementioned board for ion generation.

The invention provides an ion generating apparatus comprising:

a substrate for ion generation including:

a substrate formed of ceramics, a discharge electrode formed on one principal surface of the substrate, an induction electrode formed on the other principal surface of the substrate, a first protective layer formed so as to cover the discharge electrode on the one principal surface of the substrate, and a second protective layer formed so as to cover the induction electrode on the other principal surface of the substrate, wherein the discharge electrode and the induction electrode are disposed opposite to each other, wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and thereby positive ions and negative ions are generated in the air, and wherein porosity of the substrate is 5 to 10 vol. %;

an air fan for delivering the positive ions and negative ions generated by the board for ion generation; and a control unit for supplying high AC voltage necessary for discharge operation to the board for ion generation.

According to the invention, the board for ion generation comprises a substrate formed of ceramics; a discharge electrode formed on one principal surface of the substrate; an induction electrode formed on the other surface of the substrate; a first protective layer formed so as to cover the discharge electrode on the one principal surface of the substrate; and a second protective layer formed so as to cover the induction electrode on the other principal surface of the substrate. The discharge electrode and the induction electrode are disposed opposite to each other. In the board for ion generation, surface discharge directed from a zone above the discharge electrode toward a zone above the end of the induction electrode and surface discharge directed from the zone above the end of the induction electrode toward the zone above the discharge electrode are generated alternately on the surface of the first protective layer by applying an AC voltage between the discharge electrode and induction electrode, and positive ions and negative ions are thereby generated in the air. In the board for ion generation, the porosity of the substrate is 5 to 10 vol. %. In this way, the number of generated negative ions can be increased to not less than two times as large as that of the positive ions, without increasing significantly the number of generated positive ions per unit volume in the air. As a result, a more relaxing environment for humans can be provided in combination with the disinfecting, deodorizing and other effects.

Thus, in the board for ion generation of the invention, due to a substrate porosity of 5 to 10 vol. %, the number of generated negative ions can be greatly increased in comparison with the conventional boards, but a specific action leading to this result is unclear. However, the tests conducted by the inventors have confirmed the operation effect of the invention.

Further, it is not necessary to bias the AC voltage to the negative voltage side in order to increase the number of generated negative ions. Therefore, the increase in the generated amount of harmful ozone caused by the increase in the maximum negative voltage value can be inhibited.

Furthermore, since the discharge electrode and induction electrode are covered with the first protective layer and second protective layer, respectively, those electrodes can be protected from wear by the discharge.

Further, according to the invention, an ion generation section composed of a discharge electrode and an induction electrode is formed in a first region of the substrate, and a positive ion adsorption section is formed in a region adjacent to the ion generation section of the substrate. The positive ion adsorption section is composed of an electrostatic electrode provided on the one principal surface of the substrate, the electrostatic electrode having one surface exposed and being charged negatively and a counter electrode provided on the other principal surface and charged positively. With such a configuration, the positive ions generated by the ion generation section can be neutralized by the electrostatic electrode having the one surface exposed on the positive ion adsorption section and the negative ions can be outputted, while reducing the output of positive ions.

According to the invention, the electrostatic electrode is formed of a plurality of conductors of the same shape or formed of a conductor formed to have a net-like shape. As a result, the peripheral length of the electrostatic electrode can be greatly increased. Further, the negative electric field can be concentrated in the outer peripheral portion of the electrostatic electrode and positive ions can be adsorbed with good efficiency. Therefore, the output of positive ions can be effectively reduced and by using this board for ion generation, the number of generated negative ions can be further increased with respect to the number of generated positive ions.

Further, according to the invention, when a plurality of protrusions are formed on the one surface of the electrostatic electrode, positive ions can be effectively adsorbed because a negative electric field concentrates in the protrusions, and thus the output of positive ions can be reduced. Therefore, by using this board for ion generation, the number of generated negative ions can be reduced with respect to the number of generated positive ions.

According to the invention, since the ion generating apparatus is provided with the above-described board for ion generation, it is possible to obtain an ion generating apparatus in which the amount of generated harmful ozone is inhibited and the number of negative ions generated is remarkably increased with respect to the number of positive ions generated.

BRIEF DESCRIPTION OF THE DRAWINGS

Other and further objects, features, and advantages of the invention will be more explicit from the following detailed description taken with reference to the drawings wherein:

FIG. 1A is a plan view of the board for ion generation, and FIG. 1B is a cross-sectional view along the line A-A' in FIG. 1A;

DETAILED DESCRIPTION

Figure 1A:
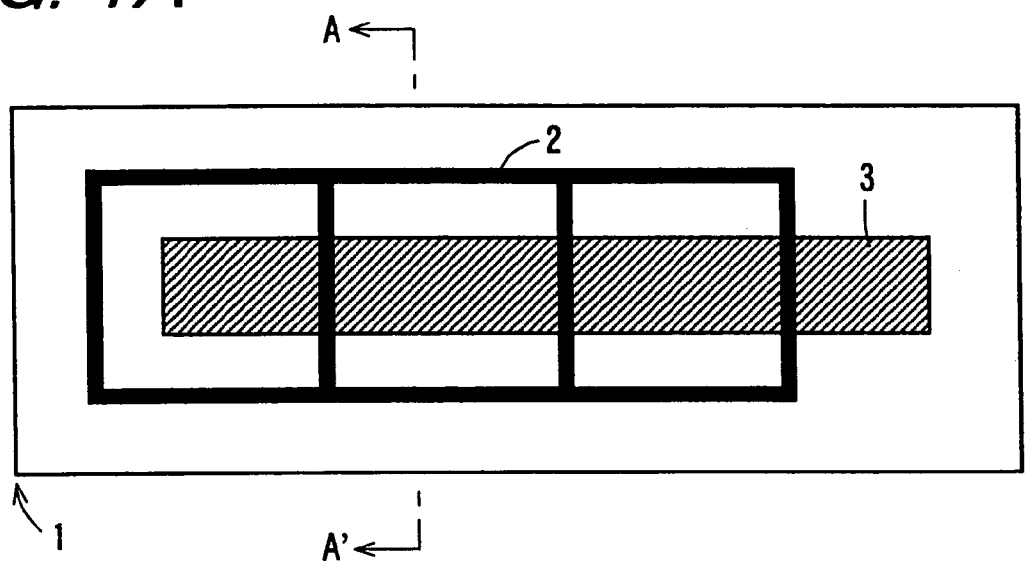
FIGS. 1A and 1B show a board for ion generation according to a first embodiment of the invention.

Now referring to the drawings, preferred embodiments of the invention are described below.

Figure 1B:
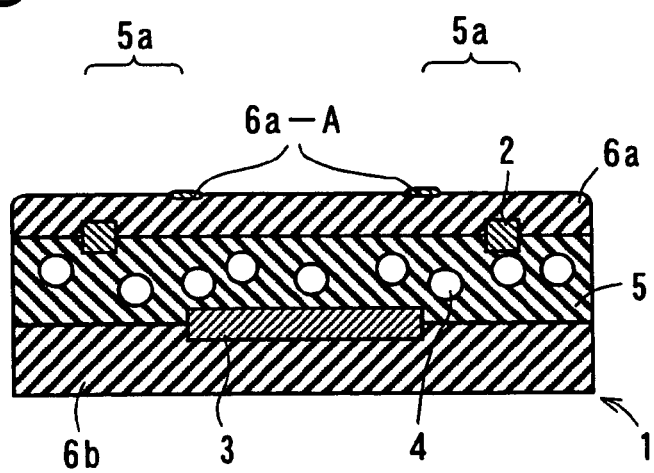

A board for ion generation of the invention is described on the basis of the drawings. FIGS. 1A and 1B are views show a board 1 for ion generation according to a first embodiment of the invention. FIG. 1A is a plan view of the board 1 for ion generation, and FIG. 1B is a cross-sectional view of the board 1 for ion generation along the line A-A' in FIG. 1A. Further, FIG. 2 is a cross-sectional view illustrating a board 1A for ion generation according to a second embodiment of the invention.

In FIGS. 1A and 1B, the board 1 for ion generation according to the first embodiment of the invention comprises a substrate 5, a discharge electrode 2, an induction electrode 3, a first protective layer 6a and a second protective layer 6b. The discharge electrode 2 is formed on one principal surface of the substrate 5. The induction electrode 3 is formed on another principal surface of the substrate 5. Here, the discharge electrode 2 and the induction electrode 3 are disposed opposite to each other. In the substrate 5, voids (pores) 4 are present. The first protective layer 6a is formed so as to cover the discharge electrode 2 on the one principal surface of the substrate 5. The second protective layer 6b is formed so as to cover the induction electrode 3 on the other principal surface of the substrate 5. An ion generating section 5a is formed by the discharge electrode 2 and the induction electrode 3. In FIG. 1A, in order to make easy understanding of the configuration of the discharge electrode 2 and the induction electrode 3 which are formed inside the board 1 for ion generation, the first protective layer 6a and the substrate 5 are illustrated as if they were formed of transparent materials. Further, the hatching portion of the induction electrode 3 does not show a cross section.

Figure 2:
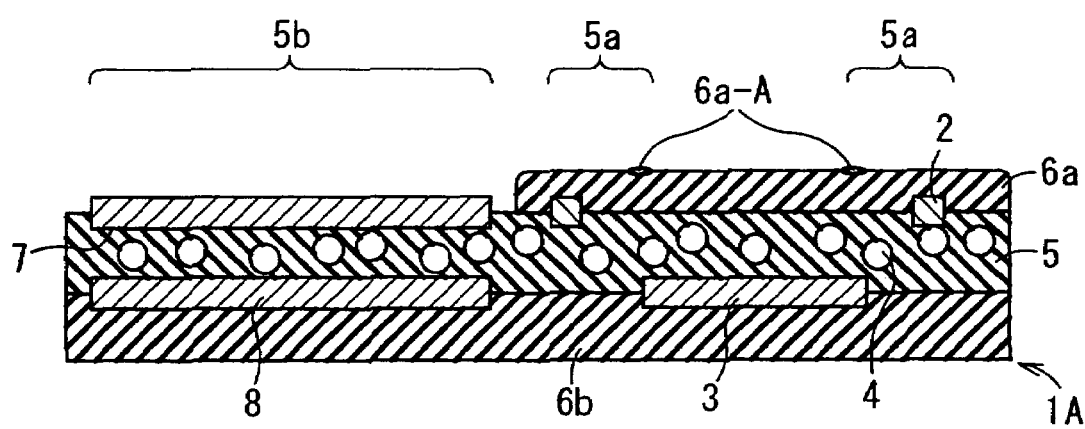
FIG. 2 is a cross-sectional view illustrating a board for ion generation according to a second embodiment of the invention.

In FIG. 2, the board 1A for ion generation according to the second embodiment of the invention comprises a substrate 5, a discharge electrode 2, an induction electrode 3, a first protective layer 6a, a second protective layer 6b, an electrostatic electrode 7 and a counter electrode 8. In the board 1A for ion generation according to the second embodiment of the invention, the constitution except the electrostatic electrode 7 and the counter electrode 8 is the same as that of the board 1 for ion generation of the first embodiment of the invention and accordingly the overlapping explanations will be omitted.

In the board 1A for ion generation of the second embodiment of the invention, the ion generating section 5a composed of the discharge electrode 2 and the induction electrode 3 is formed in a first region (a right half region of the substrate 5 in FIG. 2), and a positive ion adsorption section 5b is formed in a region adjacent to the ion generating section 5a of the substrate 5 (a left half region of the substrate 5 in FIG. 2). The positive ion adsorbing section 5b is composed of the electrostatic electrode 7 which is provided on the one principal surface of the substrate, the electrostatic electrode having one surface exposed and being charged negatively and the counter electrode 8 which is disposed on the other principal surface of the substrate 5 and is charged positively.

The substrate 5 and the first and second protective layers 6a, 6b of the invention are formed of a dielectric formed of ceramics, for example, an aluminum oxide-based sintered body (alumina ceramics). The substrate 5 has a quadrangular shape in the plan view thereof.

The discharge electrode 2 and the induction electrode 3 and also the electrostatic electrode 7 and the counter electrode 8 are composed of metalized layers formed of a metal powder with a high melting point such as W (tungsten), Mo (molybdenum), Mn (manganese) or composite of these metals. The discharge electrode 2 and the induction electrode 3 and also the electrostatic electrode 7 and the counter electrode 8 are electrically connected to an external power source with respective connection lines (not shown). The discharge electrode 2 is formed, for example, as a grid-like rectangular and the induction electrode 3' is formed as a plane-like rectangular. Each of the discharge electrode 2 and induction electrode 3 has a thickness of about 15 µm, and the electrodes are formed opposite to each other so that the central axes of the respective electrode formation regions in the longitudinal directions thereof coincide.

Further, the thickness of the electrostatic electrode 7 and the counter electrode 8 is about 15 µm, respectively, similarly to that of the discharge electrode 2 and the induction electrode 3, and have, for example, a rectangular shape.

Here, the discharge electrode 2 is formed in a grid-like shape so that a large number of linear conductors composed of metalized layers, for example, cross each other at a right angle, so as to face the induction electrode 3. Therefore, when an AC voltage is applied, surface discharge is generated from the surface portion of the first protective layer 6a where the linear conductors are located toward the discharge portion 6*a*-A in the surface of the first protective layer 6*a* located above the end of the induction electrode 3. Furthermore, when the voltage changes, surface discharge is generated from the discharge portion 6*a*-A toward the surface portion of the first protective layer 6*a* where the linear conductors of the discharge electrode 2 are located. At this time, positive and negative cluster ions are generated, due to the generation of positive ions and negative ions obtained by moisture decomposition by the surface discharge, in the air on the perimeter thereof. Further, even when the voltage sign changes, the surface discharge is generated in the opposite direction and positive and negative cluster ions are similarly generated.

Further, a DC voltage, for example, of several hundred volts is applied between the electrostatic electrode 7 shown in FIG. 2 and the counter electrode 8 so that the exposed surface of the electrostatic electrode 7 is charged negatively. Thereby, the electrostatic electrode 7 functions to adsorb, entrap and neutralize the positive ions from the air flow containing positive ions and negative ions that are generated in the ion generation unit 5*a* and passing above the electrostatic electrode.

Further, in the counter electrode 8 formed on the other principal surface of the substrate 5 opposite to the electrostatic electrode 7, the surface of the second protective layer 6*b* formed so as to cover the counter electrode surface is charged positively. However, since the air flow containing positive ions and negative ions generated by the ion generation unit 5*a* does not pass above the charged surface, the negative ions are not trapped.

Therefore, the content ratio of negative ions in the air flow passing through the positive ion adsorption section 5*b* further increases, thereby making it effective for sterilization and disinfection and also for producing a relaxing effect on humans. Therefore, it is preferred that a positive ion adsorption section 5*b* provided with the electrostatic electrode 7 and the counter electrode 8 be formed.

Further, the counter electrode 8 may be coated or not coated with the second protective layer 6*b*, but it is preferably coated with the second protective layer 6*b* in order to protect the surface of the counter electrode 8 from oxidation caused, e.g., by oxygen present in the air. Further, the electrostatic electrode 7 is so provided that the surface thereof is exposed. Therefore, in the case of long-term operation, for example, a thin film of tungsten oxide ($WO_2$) is sometimes formed on the surface. Such a thin oxide film does not cause any loss in the positive ion adsorption and neutralization effect, but in the case of successively coating a nickel (Ni) plated layer with a thickness of 1-12 µm and a gold (Au) plated layer with a thickness of about 0.3-5 µm on the surface of the electrostatic electrode 7, it is preferred that the surface of the electrostatic electrode 7 be protected to maintain fully the ion adsorption and neutralization effect.

Figure 3A:
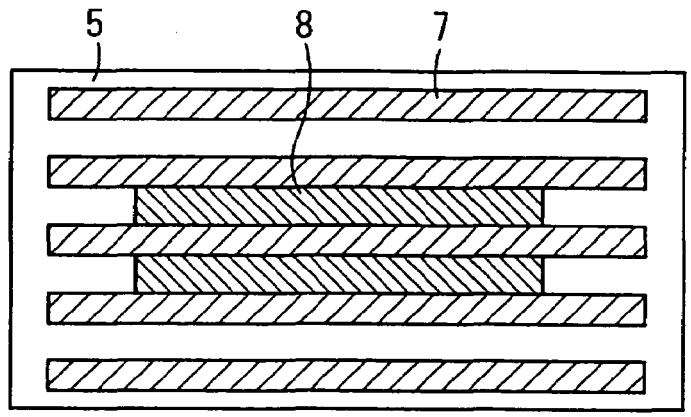
FIGS. 3A to 3C are enlarged plan views showing the electrostatic electrode illustrating a board for ion generation according to a third embodiment of the invention.
Figure 3B:
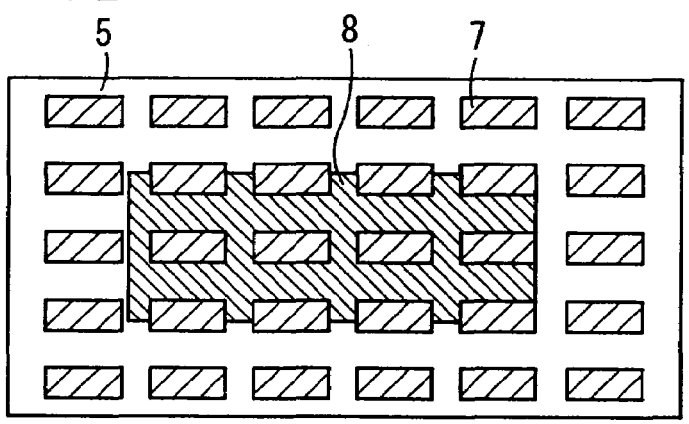
Figure 3C:
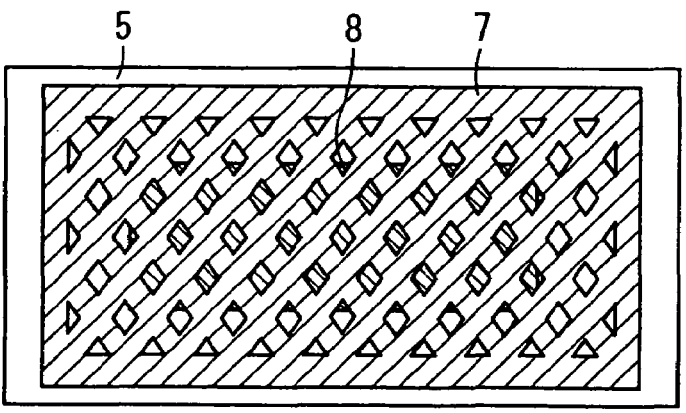

FIGS. 3A to 3C are enlarged plan views showing the electrostatic electrode illustrating a board 1A for ion generation according to a third embodiment of the invention. The electrostatic electrode 7 is preferably formed by a plurality of conductors of the same shape or from conductors formed to have a net-like shape as shown in FIGS. 3A to 3C. A plurality of conductors of the same shape or a net-like shape refer to configurations in which a plurality of linear electrostatic electrodes 7 are disposed, as shown in FIG. 3A, a plurality of quadrangular electrostatic electrodes 7 are disposed, as shown in FIG. 3B, or a net-like electrostatic electrode 7 is provided, as shown in FIG. 3C, rather than a configuration in which the electrostatic electrode 7 is provided over the entire one surface. The conductors can also have other appropriate shapes such as a triangular shape, a round shape, a polygonal shape, an irregular shape, or shapes arranged by combining those shapes.

With such a configuration, the peripheral length of the electrostatic electrode 7 can be greatly increased, thereby concentrating the negative electric field in the end portion on the outer periphery of the electrode. Therefore, positive ions can be easily adsorbed in the outer peripheral portion of the electrostatic electrode 7 and the positive ions can be efficiently adsorbed by the electrostatic electrode 7. As a result, with such a configuration, the quantity of positive ions that are outputted from the ion generating apparatus can be effectively reduced. In this way, by using this ion generating apparatus, more negative ions than positive ions can be generated.

In the configuration shown in FIG. 3A, the linear electrostatic electrodes 7 are preferably provided perpendicularly to the ion flow. This configuration allows the ion flow to pass transversely across over the electrostatic electrode 7 at all times. Accordingly, the ion flow can easily be brought into contact with the outer peripheral portion of the electrostatic electrodes 7 and positive ions can be easily trapped by the electrostatic electrodes 7. As a result, the positive ions can be adsorbed with even higher efficiency.

In the configuration shown in FIG. 3B, the quadrangular electrostatic electrodes 7 are preferably so disposed that the side thereof that is perpendicular to the ion flow is longer than the side along the ion flow direction. With such a configuration, the ion flow can easily be brought into contact with the outer peripheral portion of the electrostatic electrodes 7 and positive ions can be easily trapped by the electrostatic electrodes 7. As a result, the positive ions can be adsorbed with even higher efficiency. Further, in FIG. 3B, the quadrangular electrostatic electrodes 7 are arranged in the vertical and horizontal direction to obtain a checkerboard shape, the positive ions can be adsorbed with even higher efficiency when electrostatic electrodes are so arranged that the rows are shifted in the direction perpendicular to the ion flow direction.

Further, the electrostatic electrodes 7 preferably have a plurality of protrusions formed on the one exposed surface thereof. In such a case, the negative electric field concentrates in the protruding portions of the electrostatic electrodes 7 and, therefore, the positive ions is easily adsorbed by the electrostatic electrodes 7. As a result, the number of positive ions outputted from the ion generating apparatus can be decreased.

In order to form a plurality of protrusions on the one surface of the electrostatic electrode 7, to a metal paste for forming the electrostatic electrode 7, a metal powder that does not melt at a firing temperature of the metal paste and has a large particle size, for example, a metal powder composed of W, Mo, Mn, or the like, may be admixed. A plurality of protrusions with acute angles at the edges and a height of 10-50 µm can be formed on the surface of the electrostatic electrode 7 by admixing to the metal paste a metal powder with a large mean particle size of 10-50 µm and having acute angles in the corner portions.

Further, a large number of voids 4 are formed inside the substrate 5, the porosity of the voids 4 being 5 vol. % to 10 vol. %. When the porosity of the voids 4 is less than 5 vol. %, the efficiency of generating the negative cluster ions is degraded and the relaxing effect on humans, which is the main object of the invention, is reduced. In the case of the porosity of voids 4 being more than 10 vol. %, there are such drawbacks that the strength of the substrate 5 is reduced and that defects such as chipping or cracking can occur in the manufacturing process.

The porosity as referred to herein means a ratio of the volume of the pores (voids 4) contained in a dielectric body to the volume of the entire dielectric body. The porosity is obtained as (v/V)×100, where v represents a total volume of the pores and V represents the volume of the dielectric body, and is expressed as vol. %. The volume of individual pores actually cannot be found. Therefore, the ratio (%) of the total surface area of individual pores per unit surface area in the polished cross section is calculated, the operation is repeated the prescribed number of times in the cross section, and the average value is computed. The computation can be conducted with an image analyzer (for example, "LUZEX" manufactured by Nicore Corp.) that finds the ratio of bright and dark zones by optically binarizing the bright and dark zones of the surface.

When such a substrate 5 is composed, for example, of alumina ceramics, the boards for ion generation 1, 1A are fabricated in the manner as follows.

First, an appropriate organic binder or a plasticizer, a dispersant and a solvent are added to and mixed with the starting material powders such as alumina ($Al_2O_3$), silicon oxide ($SiO_2$), calcium oxide (CaO) and magnesium oxide (MgO) to obtain a slurry-like insulator paste. In order to form voids 4, in this process, for example, the amount of the binder added may be adjusted, the content ratio of alumina, which is the main component of the insulator paste, may be increased to inhibit sintering ability, or fine particles, e.g., of a polymer that has poor solubility in the organic solvent and is thermally decomposable at a sintering temperature of the alumina sintered body may be admixed in the slurry. The paste is molded into a sheet by a well-known conventional sheet molding method such as a doctor blade method or a calendar roll method and a green sheet of the prescribed thickness is obtained.

Then, a metallic paste comprising, for example, a tungsten (W) powder as the main component and serving to obtain the discharge electrode 2 and the induction electrode 3, and further, in the embodiment shown in FIG. 2, the electrostatic electrode 7 and the counter electrode 8 is applied by printing to both principal surfaces of the green sheet. An insulator paste composed of the same material as the insulator paste serving as the substrate 5 is printed by a screen printing method so as to cover the discharge electrode 2 and to obtain a printed layer serving as a first protective layer 6a. Then, in a similar manner, a printed layer serving as a second protective layer 6b is formed so as to cover the induction electrode 3 and the counter electrode 8, and finally the boards 1, 1A for ion generation are produced by firing at a temperature of about 1600° C. in a reducing atmosphere.

Further, since the insulator paste for the first and second protective layers 6a, 6b is not required to cause the formation of voids 4, an insulator paste having a different content ratio of alumina from that of the substrate 5 may be used, or an insulator paste without addition of the fine polymer particles may be used. Since the voids 4 are not formed in the protective layers composed of such an insulator paste, the thickness of the protective layers can be reduced.

The first protective layer 6a and the second protective layer 6b may be formed so that green sheets are stacked one on top of another. Furthermore, a metal paste serving to obtain the discharge electrode 2 and the induction electrode 3, the electrostatic electrode 7 and the counter electrode 8 may be also obtained by using a metal powder with a high melting point such as molybdenum (Mo) or manganese (Mn) instead of W, for example.

It has been found that with respect to the boards 1, 1A for ion generation of the invention that is obtained in the above-described manner, applying an AC voltage to the discharge electrode 2 and the induction electrode 3 makes increase of generation of negative ions by a factor of from about 2.2 to about 2.7 larger than that of the positive ions. Furthermore, it has been experimentally demonstrated that forming the positive ion adsorption section 5b as shown in FIG. 2 enables trapping and neutralizing about 25 to 50% of the positive ions generated in the ion generating section 5a.

Since the boards 1, 1A for ion generation of the invention can efficiently generate more negative ions than positive ions, an air state can be obtained that is produced a better relaxing effect on humans in addition to the disinfecting and deodorizing effects. Moreover, providing the positive ion adsorption section 5b where the electrostatic electrode 7 and the counter electrode 8 are disposed makes it possible to entrap and neutralize the generated positive ions. Therefore, an always clean and pleasant space can be obtained more advantageously.

Further, with the boards 1, 1A for ion generation according to the invention, the number of generated negative ions can be sufficiently increased even without biasing the AC voltage to the negative voltage side in order to increase the number of generated negative ions. Therefore, the increase in the amount of harmful ozone due to the increase in the maximum negative voltage value caused by applying the bias is prevented.

Figure 4:
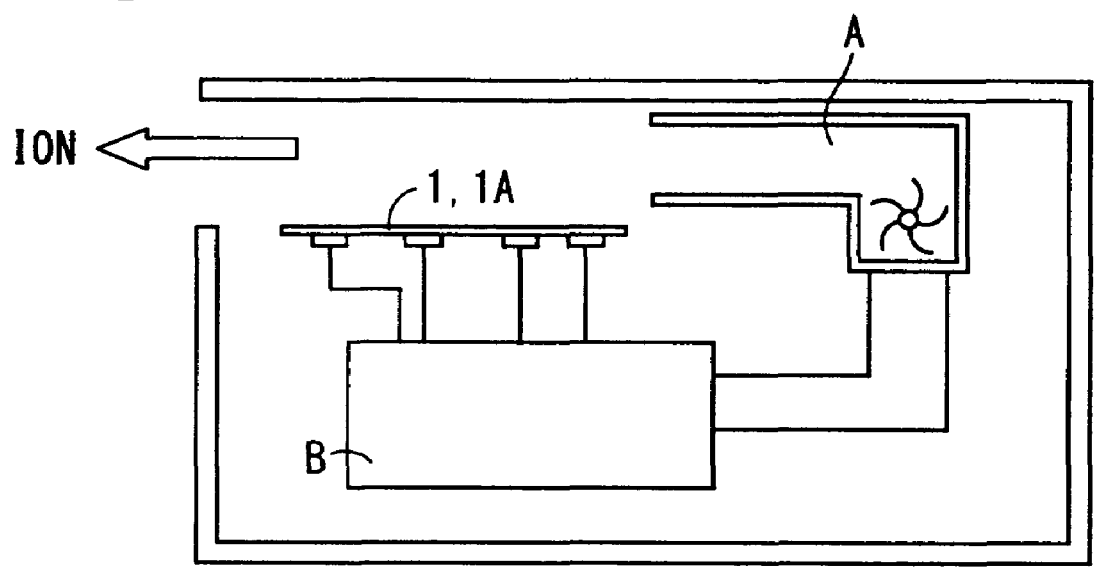
FIG. 4 is a schematic cross-sectional view illustrating an ion generating apparatus according to a fourth embodiment of the invention.

An ion generating apparatus equipped with the board 1 for ion generation of the invention will be explained below. FIG. 4 is a schematic cross-sectional view illustrating of the ion generating apparatus according to a fourth embodiment of the invention. In FIG. 4, the ion generating apparatus comprises an air fan A, a control unit B, and the boards 1, 1A for ion generation of the invention. A high AC voltage, for example, of about 8 kV, that is necessary for discharge operation in the boards 1, 1A for ion generation is supplied from the control unit B to the boards 1, 1A for ion generation. Cluster ions generated on the surfaces of the boards 1, 1A for ion generation by the application of this high AC voltage are supplied into the air with the air fan A. In this way, the ion generating apparatus of the invention is operated.

Further, when the positive ion adsorption section is formed as in the board 1A of the invention shown in FIG. 2, a DC voltage, for example, of about 200-800 V is applied between the electrostatic electrode 7 and the counter electrode 8 so that the electrostatic electrode 7 is charged negatively. Furthermore, the ion adsorption section is arranged so as to be on the side of an air outlet of the ion generating apparatus.

The ion generating apparatus of the invention is an efficient ion generating apparatus in which the number of generated negative ions is higher than that of positive ions. Furthermore, the positive ions are trapped by the positive ion adsorption section and neutralized, thereby enabling the ion generating apparatus to generate the negative ions with higher efficiency. As a result, in addition to such effects as disinfection and deodorization, an environment producing a relaxing effect on humans can be provided without increasing the generation of harmful ozone.

EXAMPLES

An example of the boards 1, 1A for ion generation of the invention will be described below.

Fabricated was a board 1 for ion generation as shown in FIGS. 1A and 1B. First, sets of substrates 5 with a width of 50 mm and a length of 15 mm were prepared to have a respective thickness of 125, 200, 300 and 400 µm, each set comprising 10 substrates. Then, a net-like discharge electrode 2 was formed, wherein the squares with one side of 6 mm and a line width of 0.5 mm were arranged continuously in a row of three in the rectangular region of 8 mm×35 mm in the vicinity of the center of one principal surface of the substrate 5. The induction electrode 3 was formed as rectangles with a length of 3 mm and a width of 30 mm on the other principal surface so as to face the discharge electrode 2. The first protective layer 6a with a thickness of 15 µm and the second protective layer 6b with a thickness of 15 µm were formed so as to cover the discharge electrode 2 and the induction electrode 3, respectively.

In the fabrication of the substrate 5 of the present example, a sintered body containing 93 wt. % $Al_2O_3$ was used to obtain a porosity of voids 4 of 6.6 to 7 vol. % in the substrate 5 after sintering, and the sintering temperature was set about 20° C. lower than the usual sintering temperature (for example, 1600° C.). As a result, firing was so conducted as to generate a large number of voids 4. These substrate samples each having a different thickness were referred to as Samples 1 to 4.

Figure 5:
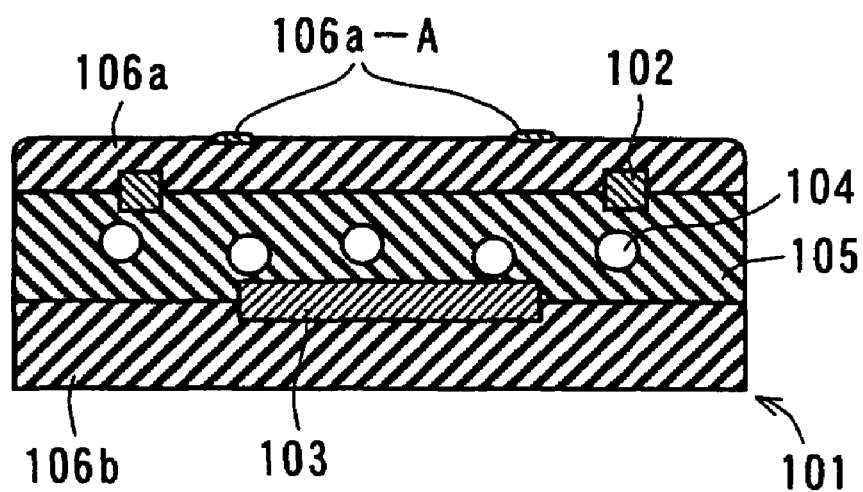
FIG. 5 is a cross-sectional view illustrating an example of a conventional board for ion generation.
Figure 6:
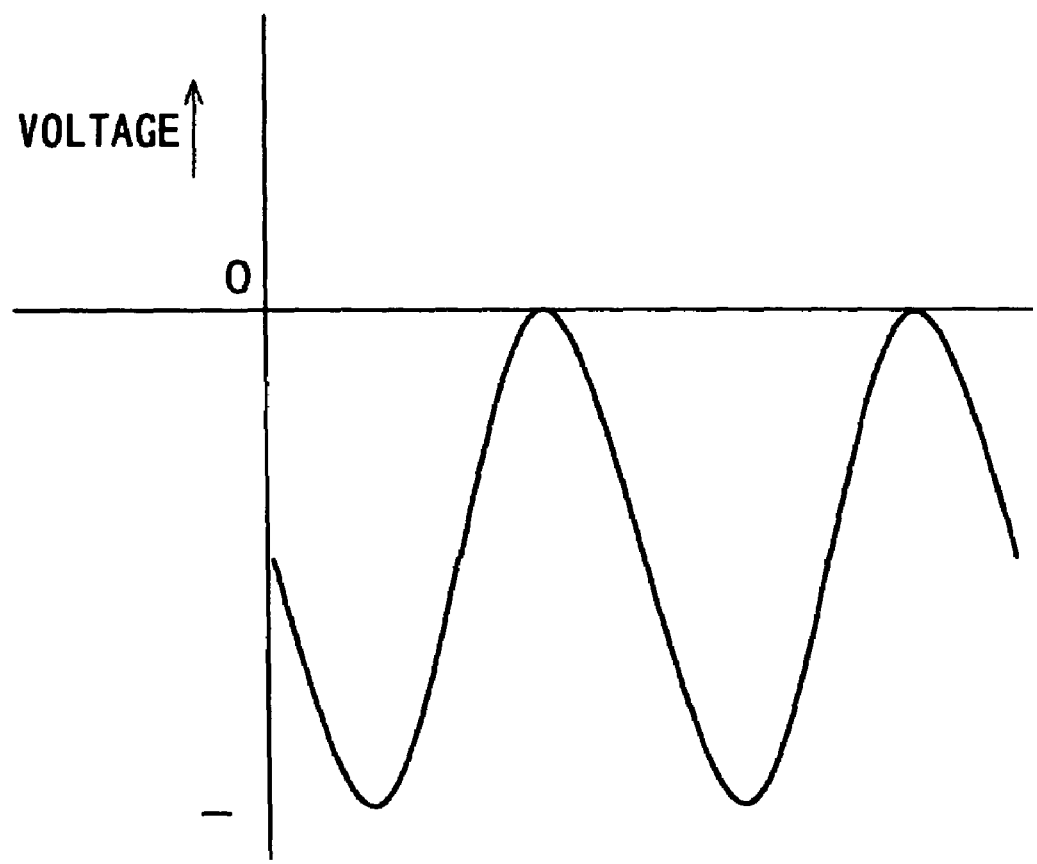
FIG. 6 is a view showing a state in which a sine waveform is biased to the negative side.

Further, for comparative evaluation, a total of 10 samples of the conventional boards 101 for ion generation, as shown in FIG. 5, were prepared as Sample 5, by fabricating a dielectric body 105 with a length of 30 mm, a width of 30 mm, a thickness of about 200 µm, and a porosity of voids 104 of about 4 vol. % and then forming the discharge electrodes 102 and the induction electrodes 103 of the same shape as the above-described discharge electrodes 2 and induction electrodes 3 and also forming the first protective layer 106a and the second protective layer 106b.

Further, the board 1 for ion generation of the invention and the conventional board 101 for ion generation were assembled in respective ion generating apparatuses, an AC voltage of 8 kV and 5 kHz was applied to the discharge electrode 2 and the induction electrode 3 of the board 1 for ion generation of the invention, and the same AC voltage was applied to the discharge electrode 102 and the induction electrode 103 of the conventional board 101 for ion generation. The number of generated positive and negative cluster ions that were produced by negative ions and positive ions generated in the vicinity of the surface of the first protective layers 6a, 106a was counted with an ion counter ("KST-900 ION TESTER" manufactured by Kobe Ion Shokai K. K.).

The results of the present example are shown in Table 1. Numerical values in the columns of Table 1 represent average values for the measurement results for 10 samples. The number of generated positive and negative cluster ions was taken as the number of generated positive ions and negative ions, respectively.

TABLE 1

| Sample No. | Thickness of dielectric body (average value) unit: µm | Number of generated negative ions unit: 1000/cm$^3$ | Number of generated positive ions unit: 1000/cm$^3$ | Porosity of voids unit: vol. % |
|---|---|---|---|---|
| 1 | 125 | 263 | 103 | 6.8 |
| 2 | 198 | 221 | 80 | 6.8 |
| 3 | 306 | 216 | 82 | 7.0 |
| 4 | 381 | 248 | 113 | 7.1 |
| 5 | 209 | 103 | 98 | 4.1 |

Data in Table 1 confirmed that the number of negative ions generated with the board 1 for ion generation of the invention was not less than 2.2 times as large as that of the positive ions. On the other hand, with the conventional board for ion generation, the number of generated negative ions was merely about 5% larger than that of the positive ions.

In order to confirm the formation state of voids 4 in the substrate 5 and voids 104 in the conventional dielectric body 105, the number of voids 4, 104 that were formed in 10 measurement locations with a surface area of 0.06 mm$^2$ per one measurement location was measured, respectively. The results demonstrated that the number of voids 104 having a size from an order of 0.1 µm to several micrometers per one measurement location was about 1400-1600, whereas in the substrate 5, this number was about 1700-2000. Recalculating this numbers as a porosity, the porosity of the conventional dielectric body 105 is 3.6 to 4.2 vol. %, whereas the porosity of the substrate 5 of the present example is 6.6 to 7 vol. %. From here it has been understood that the number of generated negative ions greatly increased with respect to the number of generated positive ions, as shown in Table 1.

Samples of the board 1 for ion generation shown in FIGS. 1A and 1B that each had a porosity of voids 4 of 4, 4.5, 5, 6, 7, 8, 9, 10 and 10.5 vol. % (the porosity was obtained by adjusting the firing conditions or by adding fine particles of a polymer to the insulator paste) and a thickness of the substrate 5 of about 200 µm were fabricated (10 samples for each porosity), the boards 1 for ion generation that were thus obtained were installed in the ion generating apparatus, and the number of generated ions was counted by the same method as described above. The results are shown in Table 2.

TABLE 2

| Porosity of voids Unit: vol. % | Number of generated negative ions unit: 1000/cm$^3$ | Number of generated positive ions unit: 1000/cm$^3$ | Notes |
|---|---|---|---|
| 3.9 | 136 | 114 | |
| 4.5 | 168 | 102 | |
| 5.2 | 229 | 98 | |
| 6.0 | 242 | 93 | |
| 7.2 | 235 | 106 | |
| 7.9 | 249 | 92 | |
| 9.1 | 250 | 117 | |
| 10.0 | 283 | 108 | |
| 10.4 | 280 | 103 | Chipping occurred in the corner of one substrate of the 10 samples |

Table 2 has demonstrated that setting the porosity of voids 4 in the board 1 for ion generation of the invention from 5 to 10 vol. % resulted in the number of generated negative ions being not less than 2.2 times as large as that of the positive ions. Furthermore, it has been found that when the porosity of voids exceeded 10 vol. %, the strength of substrate 5 was sometimes decreased and chipping defects were generated, making the substrate unsuitable for practical use.

Then, the board 1A for ion generation shown in FIG. 2 was produced by forming a positive ion adsorption section 5b provided with the electrostatic electrode 7 and the counter electrode 8 in the substrate 5. The electrostatic electrode 7 was formed in shape of a flat sheet with a length of 6 mm and a width of 12 mm and was formed in a position at a distance of 2 mm from the discharge electrode 2, and the counter electrode 8 was formed in a shape of a flat sheet with a length of 6 mm and a width of 12 mm in the position facing the electrostatic electrode 7.

Then a DC voltage of 200-800 V was applied between the electrostatic electrode 7 and the counter electrode 8, the number of generated positive ions in the point at a distance of 10 cm from the ion generating apparatus was counted, and the count was compared with the number of positive ions generated in the ion generation section 5a. The count of positive ions was 25-50% less than the number of generated positive ions in the ion generation section 5a. Thus, it has been found that the positive ion adsorption section 5b can trap and neutralize the positive ions and that the positive ion adsorption section 5b is effective. The evaluation results are shown in Table 3. Numbers in the table represent, by "%", the range of decrease ratio of the number of positive ions with respect to that obtained in the case where no voltage was applied to the positive ion adsorption section.

TABLE 3

| Magnitude of voltage applied to electrostatic electrode | Reduction ratio in the number of positive ions |
| --- | --- |
| 200 V | 25.3-27.1% |
| 400 V | 29.3-35.8% |
| 600 V | 38.0-43.3% |
| 800 V | 45.2-50.6% |

The results shown in Table 3 have demonstrated that providing the positive ion adsorption section 5b makes it possible to reduce the number of generated positive ions by 25-50% according to the voltage magnitude.

The invention is not limited to the above-described embodiments and examples, and various changes may be resorted to, without departing from the scope of the invention. For example, in the present embodiment, alumina ceramics was explained as an example of materials for the substrate 5 and the first and second protective layers 6a, 6b, but those materials are not limited to alumina ceramics, and it goes without saying that other ceramics such as aluminum nitride (AlN) ceramics, mullite ($3Al_2O_3 \cdot 2SiO_2$) ceramics or glass ceramics may be used. Furthermore, in one of the embodiments, an example of the flat board 1 for ion generation was shown, but it may also have a curved surface. Furthermore, FIGS. 1A and 1B show the discharge electrode 2 and the induction electrode 3 with straight sides, but protrusions may be disposed on the sides, or the discharge electrode 2 may have a zigzag-line contour. That is, corners may be present on the sides of the electrodes. In the case of the electrodes having such a shape, an electric field is concentrated in the corner portions. Therefore, the generation of surface discharge is facilitated and the AC voltage applied to the board 1 for ion generation can be decreased.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A board for ion generation, comprising:
 a substrate formed of ceramics;
 a discharge electrode formed on one principal surface of the substrate;
 an induction electrode formed on another principal surface of the substrate;
 a first protective layer formed so as to cover the discharge electrode on the one principal surface of the substrate; and
 a second protective layer formed so as to cover the induction electrode on the other principal surface of the substrate,
 wherein the discharge electrode and the induction electrode are disposed opposite to each other,
 wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and
 wherein porosity of the substrate is 5 to 10 vol. %.

2. A board for ion generation comprising:
 a substrate formed of ceramics;
 a discharge electrode formed on one principal surface of the substrate;
 an induction electrode formed on another principal surface of the substrate;
 a first protective layer formed so as to cover the discharge electrode on the one principal surface of the substrate; and
 a second protective layer formed so as to cover the induction electrode on the other principal surface of the substrate,
 wherein the discharge electrode and the induction electrode are disposed opposite to each other,
 wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and
 wherein porosity of the substrate is 5 to 10 vol. %,
 wherein an ion generation section composed of the discharge electrode and induction electrode is formed in a first region of the substrate, a positive ion adsorption section is formed in a region adjacent to the ion generation section of the substrate, and the positive ion adsorption section is composed of an electrostatic electrode provided on the one principal surface of the substrate, the electrostatic electrode having one surface exposed and being charged negatively and a counter electrode provided on the other principal surface of the substrate and charged positively.

3. The board for ion generation of claim 2, wherein the electrostatic electrode is formed from a plurality of conductors of a same shape or a conductor formed to have a net-like shape.

4. The board for ion generation of claim 2, wherein the electrostatic electrode has a plurality of protrusions formed on the one surface thereof.

5. The board for ion generation of claim 3, wherein the electrostatic electrode has a plurality of protrusions formed on the one surface thereof.

6. An ion generating apparatus comprising the board for ion generation of claim 1.

7. An ion generating apparatus comprising:
a substrate for ion generation including:
a substrate formed of ceramics,
a discharge electrode formed on one principal surface of the substrate,
an induction electrode formed on the other principal surface of the substrate,
a first protective layer formed so as to cover the discharge electrode on the one principal surface of the substrate, and
a second protective layer formed so as to cover the induction electrode on the other principal surface of the substrate,
wherein the discharge electrode and the induction electrode are disposed opposite to each other,
wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and
wherein porosity of the substrate is 5 to 10 vol. %;
an air fan for delivering the positive ions and negative ions generated by the board for ion generation; and
a control unit for supplying high AC voltage necessary for discharge operation to the board for ion generation.

8. An ion generating apparatus comprising:
a substrate for ion generation including:
a substrate formed of ceramics,
a discharge electrode formed on one principal surface of the substrate,
an induction electrode formed on the other principal surface of the substrate,
a first protective layer formed so as to cover the discharge electrode on the one principal surface of the substrate, and
a second protective layer formed so as to cover the induction electrode on the other principal surface of the substrate,
wherein the discharge electrode and the induction electrode are disposed opposite to each other,
wherein by applying an AC voltage between the discharge electrode and induction electrode, surface discharge directed from a zone above the discharge electrode toward a zone above an end of the induction electrode and surface discharge directed from the zone above the end of the induction electrode toward the zone above the discharge electrode are generated alternately on the surface of the first protective layer, and
wherein porosity of the substrate is 5 to 10 vol. %;
an air fan for delivering the positive ions and negative ions generated by the board for ion generation; and
a control unit for supplying high AC voltage necessary for discharge operation to the board for ion generation,
wherein an ion generation section composed of the discharge electrode and induction electrode is formed in a first region of the substrate, a positive ion adsorption section is formed in a region adjacent to the ion generation section of the substrate, and the positive ion adsorption section is composed of an electrostatic electrode provided on the one principal surface of the substrate, the electrostatic electrode having one surface exposed and being charged negatively and a counter electrode provided on the other principal surface of the substrate and charged positively.

9. The ion generating apparatus of claim 8, wherein the electrostatic electrode is formed from a plurality of conductors of a same shape or a conductor formed to have a net-like shape.

10. The ion generating apparatus of claim 8, wherein the electrostatic electrode has a plurality of protrusions formed on the one surface thereof.

11. The ion generating apparatus of claim 9, wherein the electrostatic electrode has a plurality of protrusions formed on the one surface thereof.

* * * * *